United States Patent
Neff (10) Patent No.: US 7,520,862 B2
(45) Date of Patent: Apr. 21, 2009

(54) CEREBRAL SPINAL FLUID SHUNT EVALUATION SYSTEM

(75) Inventor: Samuel Neff, Haddon Heights, NJ (US)

(73) Assignee: Neuro Diagnostic Devices, Inc., Philadelphia, PA (US)

( * ) Notice: Subject to any disclaimer, the term of this patent is extended or adjusted under 35 U.S.C. 154(b) by 251 days.

(21) Appl. No.: 10/770,754

(22) Filed: Feb. 3, 2004

(65) Prior Publication Data

US 2005/0171452 A1    Aug. 4, 2005

(51) Int. Cl.
  *A61B 5/00* (2006.01)
  *A61M 37/00* (2006.01)
  *A61M 3/00* (2006.01)
(52) U.S. Cl. .................. 600/549; 604/6.13; 604/290
(58) Field of Classification Search .......... 600/549; 604/6.13, 290
  See application file for complete search history.

(56) References Cited

U.S. PATENT DOCUMENTS

| | | | |
|---|---|---|---|
| 3,623,473 A | 11/1971 | Anderson |
| RE28,686 E | 1/1976 | Coulthard |
| 3,933,045 A | 1/1976 | Fox et al. |
| 4,206,762 A | 6/1980 | Cosman |
| 4,210,029 A | 7/1980 | Porter |
| 4,246,908 A | 1/1981 | Inagakl et al. |
| 4,255,968 A | 3/1981 | Harpster |
| 4,265,252 A | 5/1981 | Chubback et al. |
| 4,281,666 A | 8/1981 | Cosman |
| 4,281,667 A | 8/1981 | Cosman |
| 4,307,097 A | 12/1981 | Kanno et al. |
| 4,340,038 A | 7/1982 | McKean |
| 4,354,504 A | 10/1982 | Bro |
| 4,354,506 A | 10/1982 | Sakaguchi et al. |
| 4,385,636 A | 5/1983 | Cosman |
| 4,393,878 A | 7/1983 | Kahn |
| 4,441,357 A | 4/1984 | Kahn et al. |
| 4,471,786 A | 9/1984 | Inagaki et al. |

(Continued)

OTHER PUBLICATIONS

Sep. 1980, Go et al., "A Thermosensitive Device for the Evaluation of the Patency of Ventriculo-atrial Shunts in Hydrocephalus", Acta Neurochirurgica, vol. 19, pp. 209-216, Fasc. 4.

(Continued)

*Primary Examiner*—Max Hindenburg
*Assistant Examiner*—Jeffrey G Hoekstra
(74) *Attorney, Agent, or Firm*—Caesar, Rivise, Bernstein, Cohen & Pokotilow, Ltd (57) ABSTRACT

A method for evaluating cerebrospinal fluid (CSF) flow rate in a CSF shunt applied to a patient for transmitting the CSF between first and second locations of the patient includes applying temperature sensors to the CSF shunt for determining a flow rate of the CSF through the shunt to provide a determined CSF flow rate and applying an error correction sensor to the patient for providing an error correction signal. The determined CSF flow rate is adjusted in accordance with the error correction signal to provide a corrected CSF flow rate. The sensor can be a temperature sensor such as a thermistor. The CSF is cooled and a temperature value of the CSF is measured in accordance with the cooling. A time value is determined in accordance with the temperature value and the CSF flow rate is determined in accordance with the time value.

17 Claims, 4 Drawing Sheets

U.S. PATENT DOCUMENTS

| | | |
|---|---|---|
| 4,494,411 A | 1/1985 | Koschke et al. |
| 4,519,401 A | 5/1985 | Ko et al. |
| 4,548,516 A | 10/1985 | Helenowski |
| 4,564,022 A | 1/1986 | Rosenfeld et al. |
| 4,576,182 A | 3/1986 | Normann |
| 4,600,013 A | 7/1986 | Landy et al. |
| 4,608,992 A | 9/1986 | Hakim et al. |
| 4,621,647 A | 11/1986 | Loveland |
| 4,627,832 A | 12/1986 | Hooven et al. |
| 4,646,752 A | 3/1987 | Swann et al. |
| 4,648,868 A | 3/1987 | Hardwick et al. |
| 4,653,508 A | 3/1987 | Cosman |
| 4,660,568 A | 4/1987 | Cosman |
| 4,677,985 A | 7/1987 | Bro et al. |
| 4,684,367 A | 8/1987 | Schaffer et al. |
| 4,688,577 A | 8/1987 | Bro |
| 4,714,459 A | 12/1987 | Hooven |
| 4,738,267 A | 4/1988 | Lazorthes et al. |
| 4,858,619 A | 8/1989 | Toth |
| 4,971,061 A | 11/1990 | Kageyama et al. |
| 4,984,567 A | 1/1991 | Kageyama et al. |
| 4,993,425 A | 2/1991 | Kronberg |
| 4,995,401 A | 2/1991 | Bunegin et al. |
| 5,054,497 A | 10/1991 | Kapp et al. |
| 5,074,310 A | 12/1991 | Mick |
| 5,117,835 A | 6/1992 | Mick |
| 5,117,836 A | 6/1992 | Millar |
| 5,189,018 A | 2/1993 | Goldman et al. |
| 5,191,898 A | 3/1993 | Millar |
| 5,257,630 A | 11/1993 | Broitman et al. |
| 5,291,899 A | 3/1994 | Watanabe et al. |
| 5,325,865 A | 7/1994 | Beckman et al. |
| 5,409,005 A | 4/1995 | Blssonnette et al. |
| 5,494,822 A | 2/1996 | Sadri |
| 5,579,774 A | 12/1996 | Miller et al. |
| 5,617,873 A | 4/1997 | Yost et al. |
| 5,682,899 A * | 11/1997 | Nashef et al. ............... 600/505 |
| 5,683,357 A | 11/1997 | Magram |
| 5,692,514 A | 12/1997 | Bowman |
| 5,716,386 A | 2/1998 | Ward et al. |
| 5,873,840 A | 2/1999 | Neff |
| 5,919,144 A | 7/1999 | Bridger et al. |
| 5,951,477 A | 9/1999 | Ragauskas et al. |
| 5,993,398 A | 11/1999 | Alperin |
| 6,030,358 A | 2/2000 | Odland |
| 6,033,366 A | 3/2000 | Brockway et al. |
| 6,086,533 A | 7/2000 | Madsen et al. |
| 6,113,553 A | 9/2000 | Chubbuck |
| 6,117,089 A | 9/2000 | Sinha |
| 6,210,346 B1 | 4/2001 | Hall et al. |
| 6,231,509 B1 | 5/2001 | Johnson et al. |
| 6,245,027 B1 | 6/2001 | Alperin |
| 6,248,080 B1 | 6/2001 | Miesel et al. |
| 6,260,968 B1 | 7/2001 | Stark et al. |
| 6,283,934 B1 | 9/2001 | Borgesen |
| 6,296,654 B1 | 10/2001 | Ward |
| 6,309,354 B1 | 10/2001 | Madsen et al. |
| 6,328,694 B1 | 12/2001 | Michaeli |
| 6,364,899 B1 | 4/2002 | Dobak, III |
| 6,379,308 B1 | 4/2002 | Brockway et al. |
| 6,379,331 B2 | 4/2002 | Barbut et al. |
| 6,383,159 B1 | 5/2002 | Saul et al. |
| 6,390,989 B1 | 5/2002 | Denninghoff |
| 6,410,537 B1 | 6/2002 | Tortella et al. |
| 6,413,227 B1 | 7/2002 | Yost et al. |
| 6,413,233 B1 | 7/2002 | Sites et al. |
| 6,475,147 B1 | 11/2002 | Yost et al. |
| 6,492,407 B2 | 12/2002 | Brenner et al. |
| 6,500,809 B1 | 12/2002 | Frazer |
| 6,527,798 B2 | 3/2003 | Ginsburg et al. |
| 6,533,733 B1 | 3/2003 | Ericson et al. |
| 6,537,232 B1 | 3/2003 | Kucharczyk et al. |
| 6,547,734 B2 | 4/2003 | Madsen et al. |
| 6,558,336 B2 | 5/2003 | Collins |
| 6,575,928 B2 | 6/2003 | Saul et al. |
| 6,585,677 B2 | 7/2003 | Cowan, Jr. et al. |
| 6,589,189 B2 | 7/2003 | Meyerson et al. |
| 6,620,188 B1 | 9/2003 | Ginsburg et al. |
| 6,669,661 B1 | 12/2003 | Yee |
| 6,682,491 B2 | 1/2004 | Johnson |
| 6,683,530 B1 | 1/2004 | Wang |
| 6,699,269 B2 | 3/2004 | Khanna |
| 6,702,743 B2 | 3/2004 | Michaeli |
| 6,740,048 B2 | 5/2004 | Yost et al. |
| 6,746,410 B2 | 6/2004 | Yost et al. |
| 6,758,832 B2 | 7/2004 | Barbut et al. |
| 6,761,695 B2 | 7/2004 | Yost et al. |
| 6,773,407 B2 | 8/2004 | Yost et al. |
| 6,849,072 B2 | 2/2005 | Lee et al. |
| 6,875,176 B2 | 4/2005 | Mourad et al. |
| 6,875,192 B1 | 4/2005 | Saul et al. |
| 6,905,474 B2 | 6/2005 | Borgesen |
| 6,923,799 B1 | 8/2005 | Asfora |
| 6,932,787 B2 | 8/2005 | Cowan et al. |
| 7,004,961 B2 | 2/2006 | Wong et al. |
| 7,014,624 B2 | 3/2006 | Meythaler et al. |
| 7,025,727 B2 | 4/2006 | Brockway et al. |
| 7,025,739 B2 | 4/2006 | Saul |
| 2001/0020159 A1 | 9/2001 | Barbut et al. |
| 2001/0027335 A1 | 10/2001 | Meyerson et al. |
| 2001/0039386 A1 | 11/2001 | Johnson |
| 2002/0035331 A1 | 3/2002 | Brockway et al. |
| 2002/0052550 A1 | 5/2002 | Madsen et al. |
| 2002/0095087 A1 | 7/2002 | Mourad et al. |
| 2002/0128569 A1 | 9/2002 | Collins |
| 2002/0161304 A1 | 10/2002 | Eide |
| 2002/0183650 A1 | 12/2002 | Johnson |
| 2002/0198579 A1 | 12/2002 | Khanna |
| 2003/0004495 A1 | 1/2003 | Saul |
| 2003/0013956 A1 | 1/2003 | Michaeli |
| 2003/0032915 A1 | 2/2003 | Saul |
| 2003/0044055 A1 | 3/2003 | Park et al. |
| 2003/0060711 A1 | 3/2003 | Michaeli |
| 2003/0100845 A1 | 5/2003 | Eide |
| 2003/0171693 A1 | 9/2003 | Yost et al. |
| 2003/0191409 A1 | 10/2003 | Yost et al. |
| 2003/0191410 A1 | 10/2003 | Yost et al. |
| 2003/0191411 A1 | 10/2003 | Yost et al. |
| 2003/0199784 A1 | 10/2003 | Lenhardt |
| 2003/0216666 A1 | 11/2003 | Ericson et al. |
| 2004/0010208 A1 | 1/2004 | Ayad |
| 2004/0024358 A1 | 2/2004 | Meythaler et al. |
| 2004/0030278 A1 | 2/2004 | Cowan, Jr. et al. |
| 2004/0049105 A1 | 3/2004 | Crutchfield et al. |
| 2004/0057901 A1 | 3/2004 | Morita |
| 2004/0068201 A1* | 4/2004 | Saul ............................ 600/561 |
| 2004/0081949 A1 | 4/2004 | Lakin et al. |
| 2004/0082900 A1 | 4/2004 | Luttich |
| 2004/0087871 A1 | 5/2004 | Ragaukas |
| 2004/0092908 A1 | 5/2004 | Harper et al. |
| 2004/0092909 A1 | 5/2004 | Harper et al. |
| 2004/0102761 A1 | 5/2004 | Ahmed |
| 2004/0127813 A1 | 7/2004 | Schwamm |
| 2004/0138728 A1 | 7/2004 | Wong et al. |
| 2004/0142905 A1 | 7/2004 | Wang |
| 2004/0158161 A1 | 8/2004 | Lemaire |
| 2004/0211415 A1 | 10/2004 | Lurie |
| 2004/0211416 A1 | 10/2004 | Lurie |
| 2004/0230124 A1 | 11/2004 | Querfurth |
| 2004/0243058 A1 | 12/2004 | Barbut et al. |
| 2004/0243145 A1 | 12/2004 | Bobo, Sr. et al. |
| 2004/0246441 A1 | 12/2004 | Stark et al. |
| 2005/0015009 A1 | 1/2005 | Mourad et al. |
| 2005/0033171 A1 | 2/2005 | Stergiopoulos et al. |

| | | |
|---|---|---|
| 2005/0038342 A1 | 2/2005 | Mozayeni et al. |
| 2005/0090761 A1* | 4/2005 | Carney ................ 600/549 |
| 2005/0119602 A1 | 6/2005 | Murphy et al. |
| 2005/0171452 A1 | 8/2005 | Neff |
| 2005/0187488 A1 | 8/2005 | Wolf |
| 2006/0020224 A1 | 1/2006 | Geiger |
| 2006/0020239 A1 | 1/2006 | Geiger et al. |
| 2006/0034730 A1 | 2/2006 | Beyette, Jr. et al. |
| 2006/0052737 A1 | 3/2006 | Bertrand et al. |
| 2006/0057065 A1 | 3/2006 | Wang |
| 2006/0079773 A1 | 4/2006 | Mourad et al. |

OTHER PUBLICATIONS

Stein et al., "A Noninvasive Approach to Quantitative Measurement of Flow through CSF Shunts", Journal of Neurosurgery, Apr. 1981; 54(4):556-558.

Dec. 1979, Stein et al., "Noninvasive Test of Cerebrospinal Shunt Function", Surgical Forum, 30:442-442, 1979.

Stein, "Testing Cerebrospinal Fluid Shunt Function: A Noninvasive Technique", Neurosurgery, Jun. 1980 6(6):649-651.

* cited by examiner

CEREBRAL SPINAL FLUID SHUNT EVALUATION SYSTEM

BACKGROUND OF THE INVENTION

1. Field of Invention

This invention relates to cerebrospinal fluid shunts and, more particularly, to apparatus and methods for quantitatively detecting the flow of cerebrospinal fluid in such shunts non-invasively.

2. Description of Related Art

A cerebrospinal fluid (CSF)shunt includes a system of tubing that allows CSF to flow from a patient's brain to another part of the body (e.g., abdomen to relieve pressure in the spinal column). As a result, it is desirable to know, periodically, that the pathway of the CSF shunt remains unobstructed to permit CSF flow and what the flow rate is. It is also desirable to make these determinations non-invasively when quantifying the CSF flow.

The following describe different apparatus and methodologies that have been used to monitor, determine or treat body fluid flow, including CSF flow through a shunt.

"A Thermosensitive Device for the Evaluation of the Patency of Ventriculo-atrial Shunts in Hydrocephalus", by Go et al. (Acta Neurochirurgica, Vol. 19, pages 209-216, Fasc. 4) discloses the detection of the existence of flow in a shunt by placement of a thermistor and detecting means proximate the location of the shunt and the placement of cooling means downstream of the thermistor. The downstream thermistor detects the cooled portion of the CSF fluid as it passes from the region of the cooling means to the vicinity of the thermistor, thereby verifying CSF flow. However, among other things, the apparatus and method disclosed therein fails to teach or suggest an apparatus/method for quantifying the flow of the fluid through the shunt.

In "A Noninvasive Approach to Quantitative Measurement of Flow through CSF Shunts" by Stein et al., Journal of Neurosurgery, 1981, April; 54(4):556-558, a method for quantifying the CSF flow rate is disclosed. In particular, a pair of series-arranged thermistors is positioned on the skin over the CSF shunt, whereby the thermistors independently detect the passage of a cooled portion of the CSF fluid. The time required for this cooled portion to travel between the thermistors is used, along with the shunt diameter, to calculate the CSF flow rate. See also "Noninvasive Test of Cerebrospinal Shunt Function," by Stein et al., Surgical Forum 30:442-442, 1979; and "Testing Cerebropspinal Fluid Shunt Function: A Noninvasive Technique," by S. Stein, Neurosurgery, 1980 Jun. 6(6): 649-651. However, the apparatus/method disclosed therein suffers from, among other things, variations in thermistor signal due to environmental changes.

U.S. Pat. No. 4,548,516 (Helenowski) discloses an apparatus for indicating fluid flow through implanted shunts by means of temperature sensing. In particular, the apparatus taught by Helenowski comprises a plurality of thermistors mounted on a flexible substrate coupled to a rigid base. The assembly is placed on the skin over the implanted shunt and a portion of the fluid in the shunt is cooled upstream of the assembly. The thermistors detect the cooled portion of the fluid as it passes the thermistor assembly and the output of the thermistor is applied to an analog-to-digital converter for processing by a computer to determine the flow rate of the shunt fluid.

U.S. Pat. No. 6,413,233 (Sites et al.) discloses several embodiments that utilize a plurality of temperature sensors on a patient wherein a body fluid (blood, saline, etc.) flow is removed from the patient and treated, e.g., heated or cooled, and then returned to the patient. See also U.S. Pat. No. 5,494,822 (Sadri). U.S. Pat. No. 6,527,798 (Ginsburg et al.) discloses an apparatus/method for controlling body fluid temperature and utilizing temperature sensors located inside the patient's body.

U.S. Pat. No. 5,692,514 (Bowman) discloses a method and apparatus for measuring continuous blood flow by inserting a catheter into the heart carrying a pair of temperature sensors and a thermal energy source. See also U.S. Pat. No. 4,576,182 (Normann).

U.S. Pat. No. 4,684,367 (Schaffer et al.) discloses an ambulatory intravenous delivery system that includes a control portion of an intravenous fluid that detects a heat pulse using a thermistor to determine flow rate.

U.S. Pat. No. 4,255,968 (Harpster) discloses a fluid flow indicator which includes a plurality of sensors placed directly upon a thermally-conductive tube through which the flow passes. In Harpster a heater is located adjacent to a first temperature sensor so that the sensor is directly within the sphere of thermal influence of the heater.

U.S. Pat. No. 3,933,045 (Fox et al.) discloses an apparatus for detecting body core temperature utilizing a pair of temperature sensors, one located at the skin surface and another located above the first sensor wherein the output of the two temperature sensors are applied to a differential amplifier heater control circuit. The control circuit activates a heat source in order to drive the temperature gradient between these two sensors to zero and thereby detect the body core temperature.

U.S. Pat. No. 3,623,473 (Andersen) discloses a method for determining the adequacy of blood circulation by measuring the difference in temperature between at least two distinct points and comparing the sum of the detected temperatures to a reference value.

U.S. Pat. No. 3,762,221 (Coulthard) discloses an apparatus and method for measuring the flow rate of a fluid utilizing ultrasonic transmitters and receivers.

U.S. Pat. No. 4,354,504 (Bro) discloses a blood-flow probe that utilizes a pair of thermocouples that respectively detect the temperature of a hot plate and a cold plate (whose temperatures are controlled by a heat pump. The temperature readings are applied to a differential amplifier. Energization of the heat pump is controlled by a comparator that compares a references signal to the differential amplifier output that ensures that the hot plate does not exceed a safety level during use.

All references cited herein are incorporated herein by reference in their entireties.

BRIEF SUMMARY OF THE INVENTION

A method for evaluating cerebrospinal fluid (CSF) flow rate in a CSF shunt applied to the body of a patient for transmitting the CSF between first and second locations of the body includes the steps of applying a plurality of temperature sensors to the CSF shunt for determining a flow rate of the CSF through the shunt to provide a determined CSF flow rate and applying an error correction sensor to the body of the patient for providing an error correction signal. The CSF flow rate determination is adjusted in accordance with the error correction signal to provide a corrected CSF flow rate. The sensor can be a temperature sensor such as a thermistor. The CSF is cooled and a temperature value of the CSF is measured in accordance with the cooling. A time value is determined in accordance with the temperature value and the CSF flow rate is determined in accordance with the time value. The CSF flow rate can be determined in accordance with a plurality of temperature values. A temperature correction value can be determined using the error correction sensor. The temperature correction value can be a background temperature value and the corrected CSF flow rate can be provided in accordance with the temperature correction value.

BRIEF DESCRIPTION OF SEVERAL VIEWS OF THE DRAWINGS

The invention will be described in conjunction with the following drawings in which like reference numerals designate like elements and wherein.

DETAILED DESCRIPTION OF THE INVENTION

Figure 1:
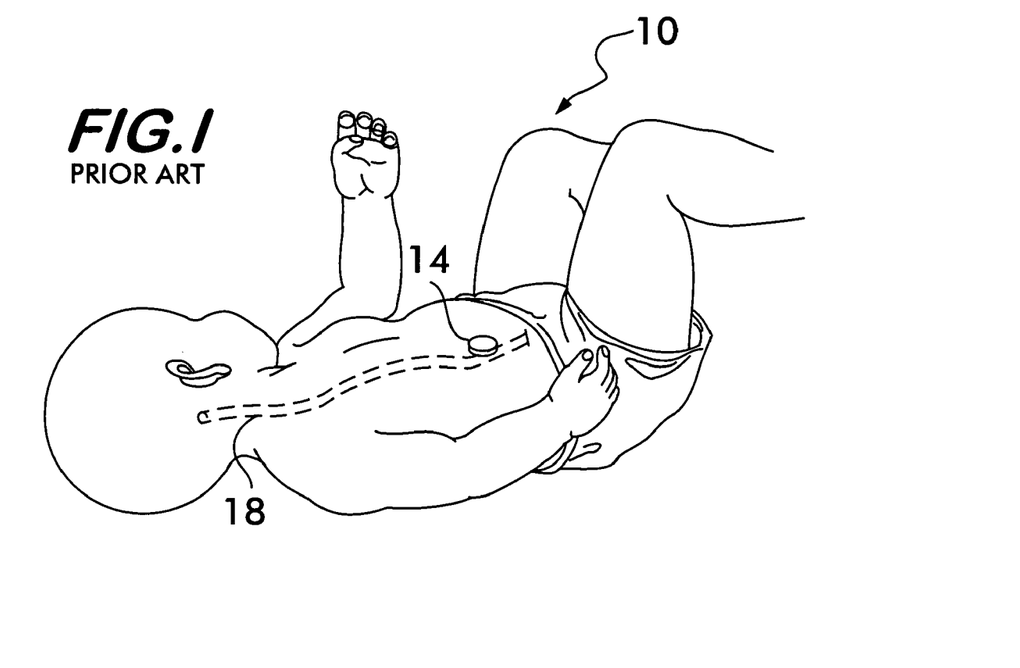
FIG. 1 shows a schematic representation of a prior art cerebral spinal fluid shunt evaluation system for monitoring the fluid flow through the shunt.

Referring now to FIG. 1, there is shown a prior art cerebral spinal fluid (CSF) shunt evaluation system 10. The CSF shunt evaluation system 10 includes a shunt tubing 18 that allows CSF to flow from the brain of a patient to another part of the body of the patient such as the abdomen, e.g., for treatment of a patient with hydroencephalus. The CSF shunt evaluation system 10 monitors the flow of the CSF through the shunt tubing 18 by means of upstream cooling of the CSF and a downstream sensor 14. The sensor 14 can be a temperature sensor, such as a thermistor, a thermocouple or a semiconductor sensor. The downstream sensor 14 is disposed over the shunt tubing 18 in the vicinity where the shunt tubing 18 empties into the abdominal cavity in order to detect changes in temperature as the cooled CSF is transported from the cooled region to the abdominal cavity.

The sensor 14 could be conventional temperature sensitive device wherein the internal resistance of the sensor 14 varies, either directly or inversely, according to the temperature of the sensor 14. Thus, changes in the temperature of the sensor 14 were detected by merely making a determination of its resistance or, equivalently, a measurement of the changes in the amount of current through the sensor 18.

In operation, a user of the shunt evaluation system 10 could place an ice cube on the scalp of the patient over the shunt tubing 18 for about one minute using, for example, forceps. While the safety of using ice makes it preferred for cooling the CSF, a Peltier stack maintained at zero or one degree centigrade can be used. The ice cube cooled the CSF in the shunt tubing 18 as it flowed from the scalp region toward the downstream sensor 14. The downstream sensor 14 was adapted to detect relatively small changes in skin temperature in regions over the shunt tubing 18 as the cooled CSF flowed from the head to the abdomen of the patient.

Figure 2:
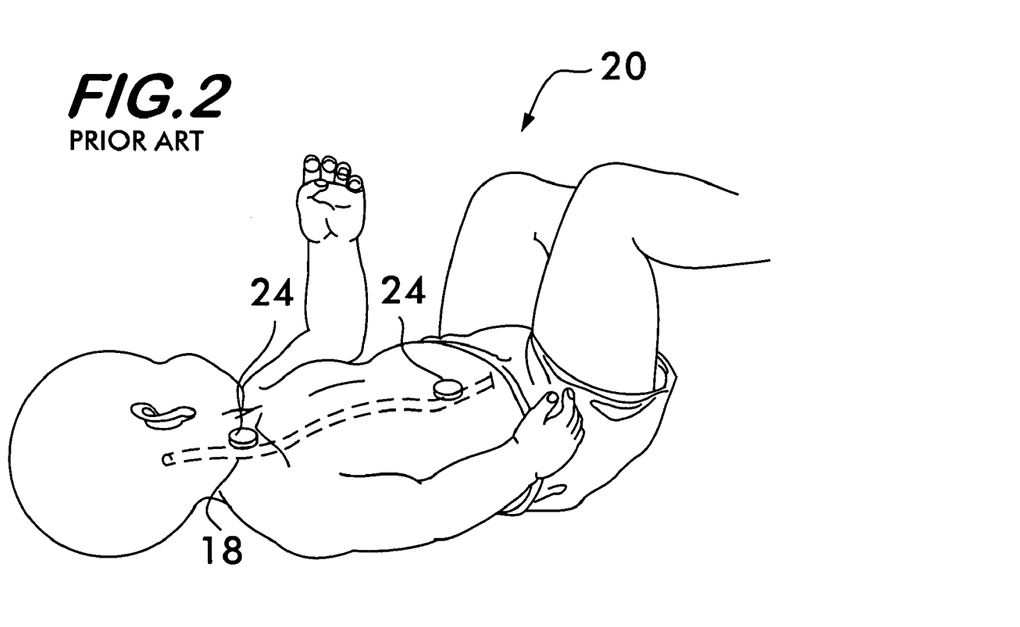
FIG. 2 shows a schematic representation of a prior cerebral spinal fluid shunt evaluation system for monitoring the fluid flow through the shunt.

Referring now to FIG. 2, there is shown a prior art CSF shunt evaluation system 20. The CSF shunt evaluation system 20 included two sensors 24 disposed over the shunt tubing 18. The two sensors 24 were separated from each other by a known distance. The use of the two sensors 24 in the shunt evaluation system 20 in this manner permitted a determination of the flow rate of the CSF through the flow of the shunt tubing 18, in addition to a determination of whether the CSF fluid was flowing through the tubing 18. The flow rate of the CSF could then be calculated since a downward temperature deflection could be recorded for each sensor 24, and the difference in time between the deflections of the two sensors 24 could be easily related to the flow velocity of the CSF.

The output of the sensors 24 in the shunt evaluation system 20 could be read and processed in any conventional manner. For example, if the internal diameter of the shunt tubing 18 was known, the rate of flow of the CSF could be calculated from the following equation:

$$F = \frac{h\pi r^2}{t_1 - t_2},$$

Where F=the flow of CFS through the shunt tubing 18, h=the distances between the two sensors 24, r=the internal radius of the shunt tubing 18 and $t_1-t_2$=the time difference between the deflection responses of the two sensors 24.

Figure 3:
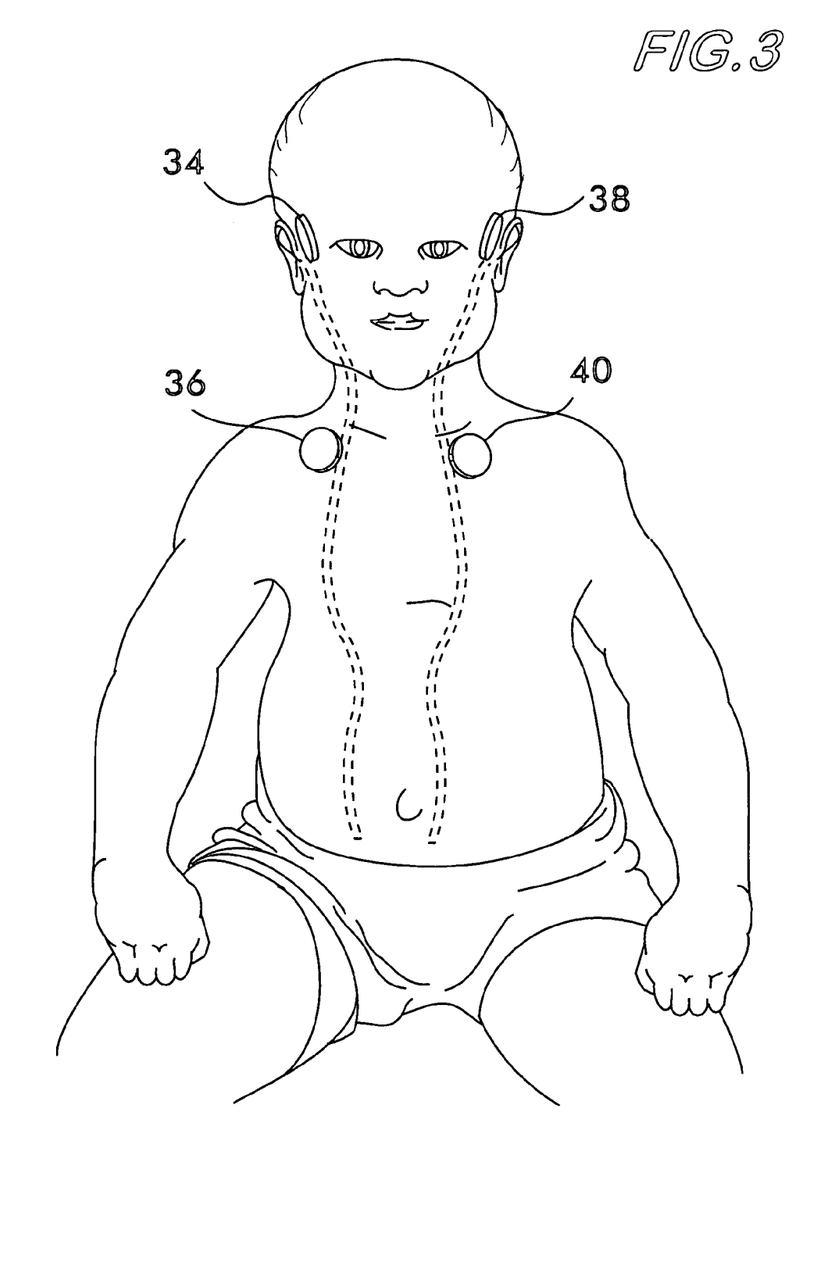
FIG. 3 shows a schematic representation of the cerebral spinal fluid shunt evaluation system of the present invention for monitoring the fluid flow through the shunt.

Referring now to FIG. 3, there is shown the CSF shunt evaluation system 30 of the present invention. The CSF shunt evaluation system 30 is provided with four sensors 34-40 disposed at predetermined locations on the body of the patient for determining the existence of CSF flow through the shunt tubing 18, and determining the flow and the flow rate of the CSF through the shunt tubing 18. Additionally, the placement of the four sensors 34-40 in the CSF shunt evaluation system 30 is adapted to permit the calculation of error signals due to background effects such as body temperature and ambient temperature. The error signals within CSF shunt evaluation system 30 can be used to provide a more accurate determination of the CSF flow rate through the shunt tubing 18.

In the method of the invention a sensor 34 is placed over the shunt tubing 18 in the vicinity of an ear of the patient for providing an electrical output signal representative of the temperature of the CSF near the vicinity of the cooling of the CSF of the patient. A sensor 36 is placed over the shunt tubing 18 in the vicinity of the clavicle of the patient for providing an electrical output signal representative of temperature of the CSF therebelow.

Preferably the sensors 34, 36 can be disposed as close as possible to each other, as long as they are placed in an area where the shunt tubing 18 is substantially close to the surface of the body. The shunt tubing 18 is usually sufficiently close to the surface behind the pinna and on the neck. It is also close to the surface over the clavicle, which is often approximately fifteen centimeters from the pinna. Thus, in one preferred embodiment of the invention the spacing between the sensors 34, 36 can be approximately fifteen centimeters or less. Furthermore, in one preferred embodiment the sensors 34, 36 can be placed as close together as approximately three centimeters.

The sensors 38, 40 are placed on the opposite side of the body of the patient in locations substantially symmetrically with the sensors 34, 36. Thus, the sensor 38 is placed in the vicinity of the ear opposite the ear where the sensor 34 is disposed. The sensor 38 is placed in the vicinity of the clavicle opposite the clavicle where the sensor 36 is disposed. The sensors 38, 40 thus provide electrical output signals representative of background conditions such as the body temperature of the patient and the ambient temperature. The output signals from the sensors 38, 40 permit control readings to be performed by the CSF evaluation system 30 for error correction of the flow rate calculations that can be obtained using the sensors 34, 36.

Figure 4:
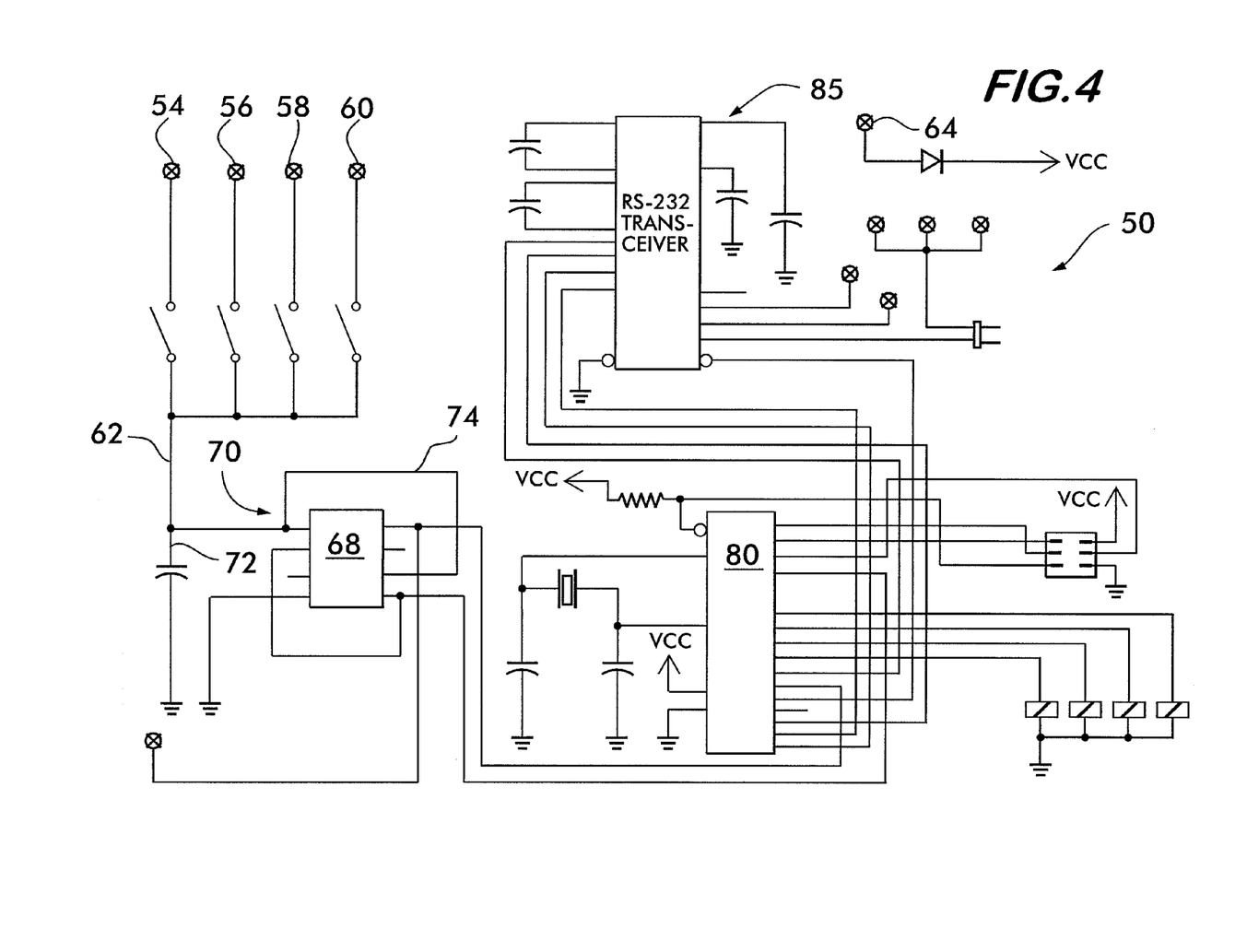
FIG. 4 shows a schematic representation of a circuit suitable for use in the cerebral spinal fluid shunt evaluation system of FIG. 3.

Referring now to FIG. 4, there is shown a schematic diagram of the shunt evaluation system circuitry 50. The shunt evaluation system circuitry 50 can be used for receiving and processing the electrical output signals provided by the sensors 34-40 of the CSF shunt evaluation system 30. The shunt evaluation system circuitry 50 processes the signals from the sensors 34-40 to provide further electrical signals representative of the temperatures of the sensors 34-40 to permit the determination of the flow rate of the CSF through the shunt tubing 18 as previously described.

The output signals of the sensors 34-40 applied to the body of the patient are received at the input lines 54-60 of the evaluation system circuitry 50. In one preferred embodiment of the invention, the signals received on the input lines 54-60 can be sequentially switched onto a common input line 62 of a general purpose precision timer 68. Additionally, in an alternate embodiment of the invention, the signals on the input lines 54-60 can be applied to an analog-to-digital converter (not shown) to provide digital signals representative of the output of the sensors 34-40 suitable for processing within the evaluation system circuitry 50.

The precision timer 68 of the evaluation system circuitry 50 that sequentially receives the signals from the sensors 34-40 is adapted to operate as a relaxation oscillator circuit 70 having a varying output frequency related to a varying RC time constant. The precision timer 68 within the relaxation oscillator circuit 70 can be the well known ICM7555 or any other equivalent device.

The precision timer 68 is coupled to a capacitor 72 and to the common input line 62 of the four input lines 54-60. Each of the sensors 34-40 coupled in sequence to the common input line 62 operates as a variable resistor whose resistance varies with a sensed temperature as previously described. The sequential coupling of the sensors 34-40 to the capacitor 72 permits RC time constant within the relaxation oscillator circuit 70 to vary when the sensors 34-40 sense different temperatures. Thus, the varying RC time constant results in varying frequencies of oscillation for the relaxation oscillator circuit 70 that correspond to the varying temperatures sensed by the sensors 34-40.

When the relaxation circuit 70 of the shunt evaluation system circuitry 50 oscillates a battery 64 charges the capacitor 72 according to the resistance of the sensor 34-40 coupled to the capacitor 72. This causes the voltage across the capacitor 72 to rise. When the voltage across the capacitor 72 rises to a predetermined level, the precision timer 62 triggers. The triggering of the precision timer 68 causes the capacitor 72 to discharge through the precision timer 62 by way of the line 74, thereby completing one cycle of the relaxation oscillator 70. The time period it takes for the capacitor 72 to charge to the predetermined voltage level and trigger is determined by the amount of charging current, and thus the amount of resistance, of the sensor 34-40 coupled to the common input line 62. Thus, the oscillation frequency of the relaxation oscillator 70 is determined by the resistance, and thus the temperature, of the active sensor 34-40.

The use of the relaxation oscillator 70 for obtaining an electrical signal representative of the resistance of the sensors 34-40 suitable for algorithmic processing is believed to be easier and less expensive than the use of an analog-to-digital converter for this purpose. Additionally, use of the relaxation oscillator 70 is believed to be more noise resistant than an analog-to-digital converter. Furthermore, the relaxation oscillator 70 uses less power than an analog-to-digital converter uses.

The frequency signal output of the precision timer 68 is applied to an input pin of a microprocessor 80 of the shunt evaluation system circuitry 50. The microprocessor 80 can be an AT90S2313 8-bit microcomputer, or any other microprocessor known to those skilled in the art. In addition to controlling the sequential switching of the sensors 34-40 onto the common input line 62, the microprocessor 80 can operate as a frequency counter to determine a frequency value in accordance with the oscillation frequency of the relaxation oscillator 70. The frequency value determined by the microprocessor 80 is provided as an output of the shunt evaluation system circuitry 50 on an output bus 85. The output bus 85 can be coupled to a conventional RS-232 transceiver. In keeping with the system of the present invention, the output frequency value can also be provided on a parallel bus.

Figure 5:
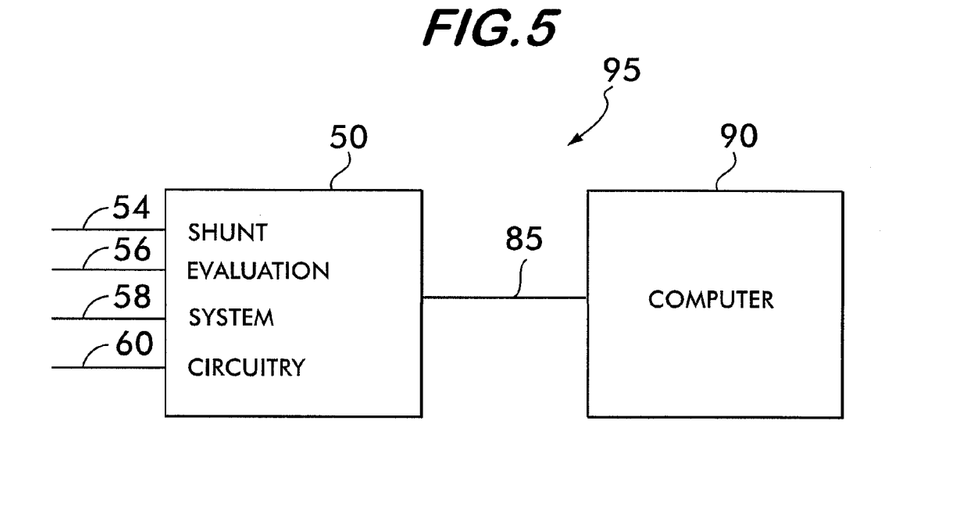
FIG. 5 shows a cerebral spinal fluid flow rate calculation system including the circuit of FIG. 4.

Referring now to FIG. 5, there is shown the CSF flow rate calculation system 95. Within the CSF flow rate calculation system 95 a computer 90 receives the frequency values determined by the shunt evaluation system circuitry 50 by way of the output bus 85. When the frequency values are received, the computer 90 performs calculations on them in order to determine the flow rate of the CSF through the shunt tubing 18 of the system 30 under the control of a stored program. Signals from the sensors 34, 36 can be used by the computer 90 to calculate the flow rate through the shunt tubing 18 as previously described. For example, the flow rate calculation set forth above with respect to the CSF shunt evaluation system 20 can then be used to determine the CSF flow rate in accordance with the determined time difference 112. Signals from one or both of the sensors 38, 40 can be used to determine an error correction signal representative of background conditions for use in correcting the calculations performed on the signals from the sensors 34, 36. One example of a stored program having algorithms suitable for performing these operations within the computer 90 is attached hereto as an Appendix.

Figure 6:
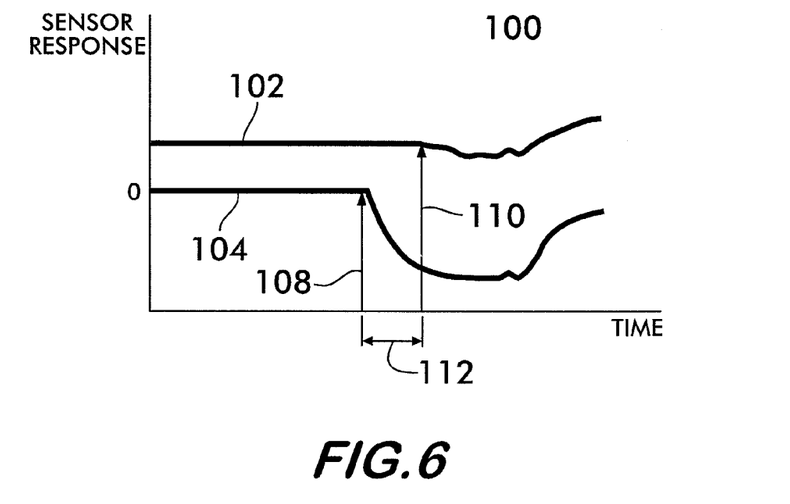
FIG. 6 shows a graphical representation of the response time of two sensors within the cerebral spinal fluid shunt evaluation system of FIG. 3.

Referring now to FIG. 6, there is shown a graphical representation 100 of the response times of the sensors 34, 36 within the CSF flow rate calculation system 95. The inflection point of the temperature inflection curve 104, representing the temperature of the sensor 34, occurs first since the cooled CSF reaches the sensor 34 first. The curve 104 inflection point occurs at time 108. At a time thereafter, varying according to the flow rate of the CSF, the inflection point of the curve 102 occurs. Curve 102 represents the temperature of the sensor 36. The temperature infection curve 102 inflection point occurs at time 110. A skilled practitioner, preferably a neurosurgeon, determines the time difference 112 between the inflection points 108, 110.

In the error correction protocol, the skin temperature at the location 38, which is the mirror-image of the location 34, is subtracted from the skin temperature at the location of sensor 34. Additionally, the skin temperature at the location of sensor 40 is subtracted from the skin temperature at the location of sensor 36. These subtractions correct for global skin temperature changes such as changes due to environment and physiology, for example excitement, attention and pain, and provide error correction for adjusting the flow rate to provide a corrected CSF flow rate.

Using the correct (subtracted) temperature curve makes it possible in a realistic clinical situation to accurately detect inflection points as the cooled CSF passes under the thermistors. When the time of the inflection pints 108, 110 and the time difference between the inflection points 108, 110 are determined the flow calculation can be performed in substantially the same manner as the flow calculations of the prior art.

For example, in one embodiment of the invention the software providing graphical representation 100 displays on the screen two temperature inflection curves 102, 104 one for the proximal (shunt temperature minus control temperature) pair of thermistors and one for the distal (shunt temperature minus control temperature) pair. The operator can use a mouse to move two vertical bars to the inflection points 108, 110.

The software can provide a window showing the times corresponding to the inflection points 108, 110 selected and prompting the operator for the diameter of the tubing. Since only two diameters are in common clinical use, the window can allow a choice between these two o in the preferred embodiment. The software then calculated the flow rate from the time difference and the diameter.

While the invention has been described in detail and with reference to specific examples thereof, it will be apparent to one skilled in the art that various changes and modifications can be made therein without departing from the spirit and scope thereof.

What is claimed is:

1. A method for evaluating an internal cerebrospinal fluid (CSF) flow rate using external measurements, said CSF flow rate occurring in a CSF shunt within a body of a patient, and said CSF shunt transmitting said CSF between differing locations of said body, the method comprising:
   (a) applying a plurality of temperature sensors to said body over said CSF shunt at exterior locations on said body to determine an externally determined CSF flow rate signal representative of said CSF flow rate to provide an externally determined CSF flow rate;
   (b) applying a background temperature sensor to said body at an exterior location on said body to determine an externally measured background induced error correction signal representative of a temperature of said exterior of said body simultaneously with said evaluating of said CSF flow rate for correcting a measurement error induced in said externally determined CSF flow rate signal by a background condition;
   (c) adjusting said CSF flow rate determination in accordance with said externally measured background induced error correction signal to provide a more accurate representation of said externally determined CSF flow rate, whereby said more accurate representation of said CSF flow rate determination is determined independently of any internally determined temperature signals provided in accordance with any temperature sensors located in the interior of said body, and whereby said CSF flow rate determination is (i) provided only according to external measurement and (ii) corrected only according to external measurement performed simultaneously with said evaluating of said externally determined CSF flow rate; and
   (d) whereby said CSF flow rate determination is provided according to a comparison of temperature values that are measured simultaneously with said evaluating of said externally determined CSF flow rate only and independently of any comparison with a predetermined control value of temperature for controlling a temperature of a fluid to make said temperature of a fluid equal to said predetermined control value of temperature.

2. A method for evaluating internal CSF flow rate in a CSF shunt applied to the body of a patient of claim 1, further comprising determining a zero CSF flow rate.

3. A method for evaluating internal CSF flow rate in a CSF shunt applied to the body of a patient of claim 1, further comprising determining a non-zero CSF flow rate.

4. A method for evaluating internal CSF flow rate in a CSF shunt applied to the body of a patient of claim 1, further comprising determining that said CSF flow rate exceeds a predetermined threshold.

5. A method for evaluating internal CSF flow rate in a CSF shunt applied to the body of a patient of claim 1, wherein said at least one temperature sensor of said plurality of temperature sensors comprises a thermistor.

6. A method for evaluating internal CSF flow rate in a CSF shunt applied to the body of a patient of claim 1, further comprising cooling said CSF.

7. A method for evaluating internal CSF flow rate in a CSF shunt applied to the body of a patient of claim 6, further comprising measuring a temperature value of said CSF in accordance with said cooling.

8. A method for evaluating internal CSF flow rate in a CSF shunt applied to the body of a patient of claim 7, further comprising determining a time value in accordance with said temperature value.

9. A method for evaluating internal CSF flow rate in a CSF shunt applied to the body of a patient of claim 8, further comprising determining said externally determined CSF flow rate in accordance with said time value.

10. A method for evaluating internal CSF flow rate in a CSF shunt applied to the body of a patient of claim 9, further comprising determining said externally determined CSF flow rate in accordance with a plurality of temperature values.

11. A method for evaluating internal CSF flow rate in a CSF shunt applied to the body of a patient of claim 7, further comprising providing a frequency signal in accordance with said measured temperature value.

12. A method for evaluating internal CSF flow rate in a CSF shunt applied to the body of a patient of claim 11, further comprising providing said frequency signal in accordance with a temperature sensor resistance.

13. A method for evaluating internal CSF flow rate in a CSF shunt applied to the body of a patient of claim 12, further comprising providing said frequency signal using an oscillator having an oscillation frequency dependent upon said temperature sensor resistance.

14. A method for evaluating internal CSF flow rate in a CSF shunt applied to the body of a patient of claim 13, wherein said oscillator comprises a relaxation oscillator.

15. A method for evaluating internal CSF flow rate in a CSF shunt applied to the body of a patient of claim 11, further comprising determining a frequency oscillation value in accordance with a measured frequency of said frequency signal.

16. A method for evaluating internal CSF flow rate in a CSF shunt applied to the body of a patient of claim 15, further comprising providing said corrected CSF flow rate in accordance with said frequency oscillation value.

17. A method for evaluating internal CSF flow rate in a CSF shunt applied to the body of a patient of claim 1, further comprising:
   applying a further background temperature sensor at an exterior location on said body for providing a further externally determined background temperature correction signal; and
   providing said corrected CSF flow rate in accordance with said further externally determined background temperature correction signal.

* * * * *